(12) United States Patent
Blomberg et al.

(10) Patent No.: US 9,671,420 B2
(45) Date of Patent: *Jun. 6, 2017

(54) AUTOMATED FLUID HANDLING SYSTEM

(71) Applicant: GE HEALTHCARE BIO-SCIENCES AB, Uppsala (SE)

(72) Inventors: Johan Blomberg, Uppsala (SE); Mats Lundkvist, Uppsala (SE)

(73) Assignee: GE HEALTHCARE BIO-SCIENCES AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/261,250

(22) Filed: Sep. 9, 2016

(65) Prior Publication Data

US 2016/0377644 A1 Dec. 29, 2016

Related U.S. Application Data

(63) Continuation of application No. 15/165,876, filed on May 26, 2016, which is a continuation of application (Continued)

(30) Foreign Application Priority Data

Jun. 9, 2009 (SE) ...................................... 0950431

(51) Int. Cl.
*B01D 35/00* (2006.01)
*B01D 15/08* (2006.01)
(Continued)

(52) U.S. Cl.
CPC ......... *G01N 35/1097* (2013.01); *B01D 15/10* (2013.01); *B01D 29/60* (2013.01);
(Continued)

(58) Field of Classification Search
None
See application file for complete search history.

(56) References Cited

U.S. PATENT DOCUMENTS

| 4,125,464 A | 11/1978 | Burger et al. |
| 5,730,867 A | 3/1998 | Drew et al. |

(Continued)

FOREIGN PATENT DOCUMENTS

| DE | 1984739 U | 5/1968 |
| DE | 1418503 A | 12/1975 |

(Continued)

OTHER PUBLICATIONS

ADE 2040 Process Analyzer Manual—Basic Operation, Applikon Analytical, Version 1.4, pp. 1-30, Jul. 2006.
(Continued)

*Primary Examiner* — Richard Gurtowski
(74) *Attorney, Agent, or Firm* — Arent Fox LLP

(57) ABSTRACT

Automated fluid handling system comprising a housing and two or more fluid handling units arranged as interchangeable modular components with an external fluidics section and an internal non fluidics section, and wherein the housing comprises a liquid handling panel with two or more of component positions for receiving said interchangeable modular components such that the external fluidics section is separated from the non fluidics section by the liquid handling panel.

30 Claims, 10 Drawing Sheets

Related U.S. Application Data

No. 14/463,039, filed on Aug. 19, 2014, now Pat. No. 9,404,902, which is a continuation of application No. 13/376,929, filed as application No. PCT/SE2010/050624 on Jun. 4, 2010, now Pat. No. 8,821,718.

(51) Int. Cl.

| | | |
|---|---|---|
| *F16K 25/00* | (2006.01) | |
| *G01N 35/10* | (2006.01) | |
| *B01D 15/10* | (2006.01) | |
| *G01N 30/88* | (2006.01) | |
| *B01D 29/60* | (2006.01) | |
| *G01N 30/24* | (2006.01) | |
| *G01N 30/38* | (2006.01) | |
| *B01D 17/12* | (2006.01) | |
| *G01N 35/00* | (2006.01) | |
| *G01N 30/02* | (2006.01) | |

(52) U.S. Cl.
CPC ............ *G01N 30/24* (2013.01); *G01N 30/38* (2013.01); *G01N 30/88* (2013.01); *B01D 15/08* (2013.01); *B01D 17/12* (2013.01); *B01D 2201/54* (2013.01); *G01N 2030/027* (2013.01); *G01N 2030/8804* (2013.01); *G01N 2030/8881* (2013.01); *G01N 2035/00326* (2013.01); *Y10T 137/6416* (2015.04); *Y10T 137/6525* (2015.04); *Y10T 137/6851* (2015.04); *Y10T 137/85986* (2015.04); *Y10T 137/87885* (2015.04)

(56) References Cited

U.S. PATENT DOCUMENTS

| | | | |
|---|---|---|---|
| 5,766,460 | A | 6/1998 | Bergstrom et al. |
| 5,896,273 | A | 4/1999 | Varghese et al. |
| 5,959,841 | A | 9/1999 | Allen et al. |
| 6,190,617 | B1 | 2/2001 | Clark et al. |
| 6,355,164 | B1 | 3/2002 | Wendell et al. |
| 6,434,018 | B1 | 8/2002 | Waltz |
| 6,599,484 | B1 | 7/2003 | Zigler et al. |
| 6,741,463 | B1 | 5/2004 | Akhtar et al. |
| 6,832,622 | B2 | 12/2004 | Hassel et al. |
| 6,968,958 | B2 | 11/2005 | Lauchner et al. |
| 7,374,674 | B2 | 5/2008 | Miyauchi et al. |
| 7,641,242 | B2 | 1/2010 | Van Pelt |
| 7,910,067 | B2 | 3/2011 | Knight et al. |
| 7,932,090 | B2 | 4/2011 | Carter et al. |
| 8,821,718 | B2 | 9/2014 | Blomberg et al. |
| 9,404,902 | B2 * | 8/2016 | Blomberg .............. G01N 30/88 |
| 2002/0185442 | A1 | 12/2002 | Maiefski et al. |
| 2004/0089057 | A1 | 5/2004 | Hobbs et al. |
| 2004/0264145 | A1 | 12/2004 | Miller et al. |
| 2005/0051468 | A1 | 3/2005 | Miyauchi et al. |
| 2006/0047466 | A1 | 3/2006 | White |
| 2006/0274082 | A1 | 12/2006 | Cochran et al. |
| 2007/0081308 | A1 | 4/2007 | Ishida |
| 2007/0097636 | A1 | 5/2007 | Johnson et al. |
| 2007/0247826 | A1 | 10/2007 | Grady et al. |
| 2008/0023653 | A1 | 1/2008 | Lee et al. |
| 2008/0035542 | A1 | 2/2008 | Mourtada et al. |
| 2008/0233653 | A1 | 9/2008 | Hess et al. |

FOREIGN PATENT DOCUMENTS

| | | |
|---|---|---|
| EP | 0309596 A1 | 4/1989 |
| JP | 2002-333438 A | 11/2002 |
| JP | 2005-106813 A | 4/2005 |
| WO | WO 00/22429 | 4/2000 |
| WO | WO 01/89681 | 11/2001 |
| WO | WO 2005/042146 A2 | 5/2005 |
| WO | WO 2006/134035 | 12/2006 |
| WO | WO 2007/036712 A1 | 4/2007 |

OTHER PUBLICATIONS

ADI 2040 Process Analyzer Manual—Analysis Methods, Applikon Analytical, Sep. 2002, pp. 1-44, Version 1.4.

ADI 2040 Process Analyzer Manual—Basic Maintenance & Spare parts, Applikon Analytical, Mar. 2008, Version 1.53, pp. 1-48.

ADI 2040 Process Analyzer Manual—Configuration, Applikon Analytical, Version 1.4, pp. 1-44, Jul. 2006.

ADI 2040 Process Analyzer Manual—Hardware & Installation, Applikon Analytical, Version 1.53, p. 144, May 2008.

ADI 2040 Process Analyzer Manual—Serial Communication, Applikon Analytical, Version 1.4, 134 pp., Apr. 2006.

ADI 2040 Process Analyzer Manual, Applikon Analytical, 1-10 pp., Apr. 1999.

ADI 2045 VA Instrument Manual, Applikon Analytical, 2007, pp. 1-80, Version 1.2.

ADI Process Analyzer Manual—Advanced Operation, Applikon Analytical, Version 1.53, pp. 1-78, Oct. 2007.

Andreas Schmid, "The Energy Issue in Whole Cell Oxyfunctionalization," GreenChem Symposium, Nov. 9, 2006, pp. 5349-5386.

APC, "Rack Enclosures and Open Frame Racks for Server and Networking Applications in It Environments," Rack Systems, 2006, pp. 4619-4638.

Applikon Analytical Confidential, "Analyzers 1999-2008," Bio-Rad Ex. 1004, Jul. 8, 2015, pp. 1323-1326.

Applikon Analytical, "Box Wet Part Module 3X," Bio-Rad Ex.1003, 1 page, Feb. 11, 2008.

Applikon Analytical, "Manual ADI 2040 Process Analyzer," Apr. 1999, Bio-Rad Ex. 1002, pp. 1-619.

Applikon Analytical, "Multi-purpose wet chemical analysis," Process Analyzer ADI 2040, Sep. 2008, pp. 1547-1554.

Applikon Analytical, "Trace Metal and Plating Bath Analysis," ADI2045VA Process Analyzer, Sep. 2007, pp. 1555-1562.

Bilsker, Petition for Inter Parties Review, *Bio-Rad Laboratories, Inc,* v. *GE Healthcare Bio-Science AB,* Sep. 2015, pp. 1-71.

Bio-Rad Laboratories, Inc., "Biologic Duoflow Chromatography System," Instruction Manual, 2003, pp. 5810-6048.

Brinkmann, "875 ProcessLab Components," ProcessLab, pp. 1-26, Mar. 2001.

Brinkmann, "875 ProcessLab Hardware," ProcessLab, pp. 1-15, Mar. 2007.

Brinkmann, "Is ProcessLab Explosion-Proof?" ProcessLab, pp. 1-12, Mar. 2001.

Dionex, "ICS-3000 Ion Chromatography System Operator's Manual," Thermo Scientific, Jan. 2008, pp. 4779-5170.

Eda Tezcanli, "An Analytical Survey on Customization At Modular Systems in the Context of Industrial Design," A Thesis Submitted to the Graduate School of Engineering and Sciences of Izmir Institute of Technology in Partial Fulfillment of the Requirements for the Degree of Master of Science in Industrial Design, Jan. 2006, pp. 5701-5809.

EP Office Action dated Feb. 26, 2014 Issued on Corresponding EP Application No. 10786454.8.

General Electric, "Operating Instructions Original Instructions," ÄKTA pure, Apr. 2014, pp. 3785-3928.

General Electric, "User Manual," ÄKTA pure, Dec. 2014, pp. 3929-4445.

Gilson, Inc., "2007-2008 Product Guide," Bio-Rad Ex. 1010 pp. 1-37.

Gilson, Inc., "402 Syringe Pump User's Guide," Bio-Rad Ex. 1011, Jun. 2001, pp. 1-86.

Gilson, Inc., "402 Syringe Pump User's Guide," Jul. 2003, pp. 5208-5293.

Gilson, Inc., "Brochure," 2003, 1 Page.

Gilson, Inc., "Gilson Product Guide," 2004, pp. 5294-5343.

Gilson, Inc., "Product Guide," The Element of Purification, Jul. 2008, pp. 5171-5207.

Gilson, Inc., "Spec Sheet," 2003, 1 Page.

Gilson, Inc., "User's Guide," 2003, 1 Page.

(56) References Cited

OTHER PUBLICATIONS

H. Schafer, "Compact View of a Modular Design or a new Philosophy in Metrohm IC," Processional IC, pp. 1-90, Sep. 2007.
J. Van Burg, "EU Declaration of Conformity," Manual ADI 2045VA, 2007, pp. 620-1322.
John Loffink, "Dell PowerEdge M1000e Modular Enclosure Architecture," Dell Enterprise White Paper, Jan. 2008, pp. 4577-4618.
JP Office Action dated Dec. 17, 2013 Issued on Corresponding JP Application No. 2012-514920.
Labomatic Instruments AG, "Customer-specific preparative HPLC Systems," 5387-5389, date unknown.
Labomatic, "Labomatic HPLC valve and column system panel," pp. 5347-5348, date unknown.
Larry Tucker et al., "Videotaped Deposition of Metrohm 30 (B) (6)," GE Healthcare vs. Bio-Rad, Aug. 10, 2015, pp. 1-292.
Metrohm—850 Processional IC Manual, http://products.matrohm.com, pp. 1-146, date unknown.
Metrohm AG, "850 Professional IC," Bio-Rad Ex. 1017, pp. 1337-1479, Feb. 2007.
Metrohm—Intelligent Ion Chromatography, www.professional-ic.com, 2012, pp. 1-28.
Metrohm Ion analysis, "IC Pump-2.872.0010," 872 Extension Module, pp. 1-67, May 2009.
Metrohm, "850 Professional IC," AnCat-MCS-2.850.3030, Bio-Rad Ex. 1017, May 2009, pp. 1-143.
Metrohm-Peak, Inc., "Determination of Anions + Oxyhalides in Various Waters by Suppressed Conductivity (USEPA method 300 A&B)," IC Application Work AW US6-0125-052007, 2007, pp. 001327-001336.
Tecan Group Ltd, "Cavro OEM Pumps and Valves," 2008, 1 page.
Tecan Group Ltd, "Cavro XLP 6000," 2008, 1 page.
Tecan Systems, "Cavro XLP 6000 Modular Syringe Pump," Operating Manual, Part I, Oct. 2005, pp. 5542-5698.
Thomas Koshy, "Declaration of Thomas Koshy," In the United States District Court for the Southern District of New York, Civil Action No. 1:14-cv-07080-LTS, pp. 1-3, Oct. 30, 2014.
United States Patent and Trademark Office, "*Bio-Rad Laboratores, Inc.*, v. *GE Healthcare Bio-Sciences AB*," Case: IPR2015-01826, U.S. Pat. No. 8,821,718 B2, Paper No. 11, Entered: Feb. 29, 2016, pp. 1-47.
United States Patent and Trademark Office, "*Bio-Rad Laboratories, Inc.* v. *GE Healthcare Bio-Sciences AB*," Declaration of Dr. Bruce Gale in Support of Bio-Rad Laboratories' Petition for Institution of an IPR on United States Patent No. 8,821,718, pp. 1-84, Sep. 2015.
Waters Corporation, "Waters 2767 Sample Manager, Injector, and Collector," Installation and Maintenance Guide, 2006, pp. 5390-5541.
Metrohm 850 Professional IC teardown system, (2.850.2220 ProfIC Anion MCS HP Gradient), Aug. 2016, pp. 1-9.
European Search Report dated Mar. 27, 2017 issued in corresponding European Patent Application No. 16205536.2. (8 pages).

\* cited by examiner

AUTOMATED FLUID HANDLING SYSTEM

CROSS REFERENCE TO RELATED APPLICATION

This application is a Continuation of U.S. patent application Ser. No. 15/165,876 filed May 26, 2016 which is a Continuation of U.S. patent application Ser. No. 14/463,039 filed Aug. 19, 2014 (now U.S. Pat. No. 9,404,902) which is a Continuation of U.S. patent application Ser. No. 13/376,929 (now U.S. Pat. No. 8,821,718) filed Dec. 8, 2011 which is a 35 U.S.C. §371 National Phase of International Patent Application No. PCT/SE2010/050624 filed Jun. 4, 2010 which claims priority to Swedish Patent Application No. 0950431-7 filed Jun. 9, 2009, the disclosure of these prior applications are hereby incorporated in their entirety by reference

BACKGROUND OF THE INVENTION

The present invention relates to the art of fluid handling system systems, and in particular to an automated fluid handling system that is highly flexible and configurable. The fluid handling system may e.g. be a liquid chromatography system, a filtration system, a chemical synthesis system or the like.

There is a large range of fluid handling systems e.g. in laboratories. Such systems comprise a number of fluid handling units, e.g. one or more pumps, valves, mixers, sensor units etc of different types. Said fluid handling units are interconnected by fluid conduits in the form of, rigid or flexible tubes or the like. Even though some systems may be designed for a specific type of application with a specific flow path, there often exists a need for flexibility and ability to alter or optimize the fluid flow path of the system. Moreover, upgrading is often restricted to specific kits provided by the manufacturer, and upgrade kits often is supplied as external add-on equipment to be arranged besides the original system, thus enlarging the foot print of the system and that need to be connected to the system both fluidically and electrically (i.e. to a system control bus or the like). Moreover, replacement of defect fluid handling units is a time consuming and delicate task.

One type of liquid handling system is liquid chromatography systems which is a standard method in laboratories, and there are a broad range of liquid chromatography systems available on the market. Common to most of the present systems is the lack of flexibility in adapting the instrument to a variety of different applications.

SUMMARY OF THE INVENTION

The object of the invention is to provide a new fluid handling system, which system overcomes one or more drawbacks of the prior art. This is achieved by the fluid handling system as defined in the independent claims.

One advantage with such a fluid handling systems is that the system may easily be upgraded without need for add-on equipment, and that the flow path may be easily optimized for new experimental setups.

Embodiments of the invention are defined in the dependent claims.

BRIEF DESCRIPTION OF THE DRAWINGS

The invention will be described in detail below with reference to the drawings, in which.

DETAILED DESCRIPTION OF THE INVENTION

According to one embodiment, there is provided an automated fluid handling system comprising a housing and two or more fluid handling units arranged as interchangeable modular components with an external fluidics section and an internal non fluidics section, and wherein the housing comprises a liquid handling panel with two or more of component positions for receiving said interchangeable modular components such that the external fluidics section is separated from the non fluidics section by the liquid handling panel.

According to another embodiment, there is provided a fluid handling system in the form of a liquid chromatography system comprising a housing, two or more high pressure pumps, at least one sensor unit and a plurality of fluid control valves of at least two different configurations, wherein at least the fluid control valves are arranged as interchangeable modular components and the housing comprises a liquid handling panel with a plurality of component positions for receiving said modular components.

Figure 1:
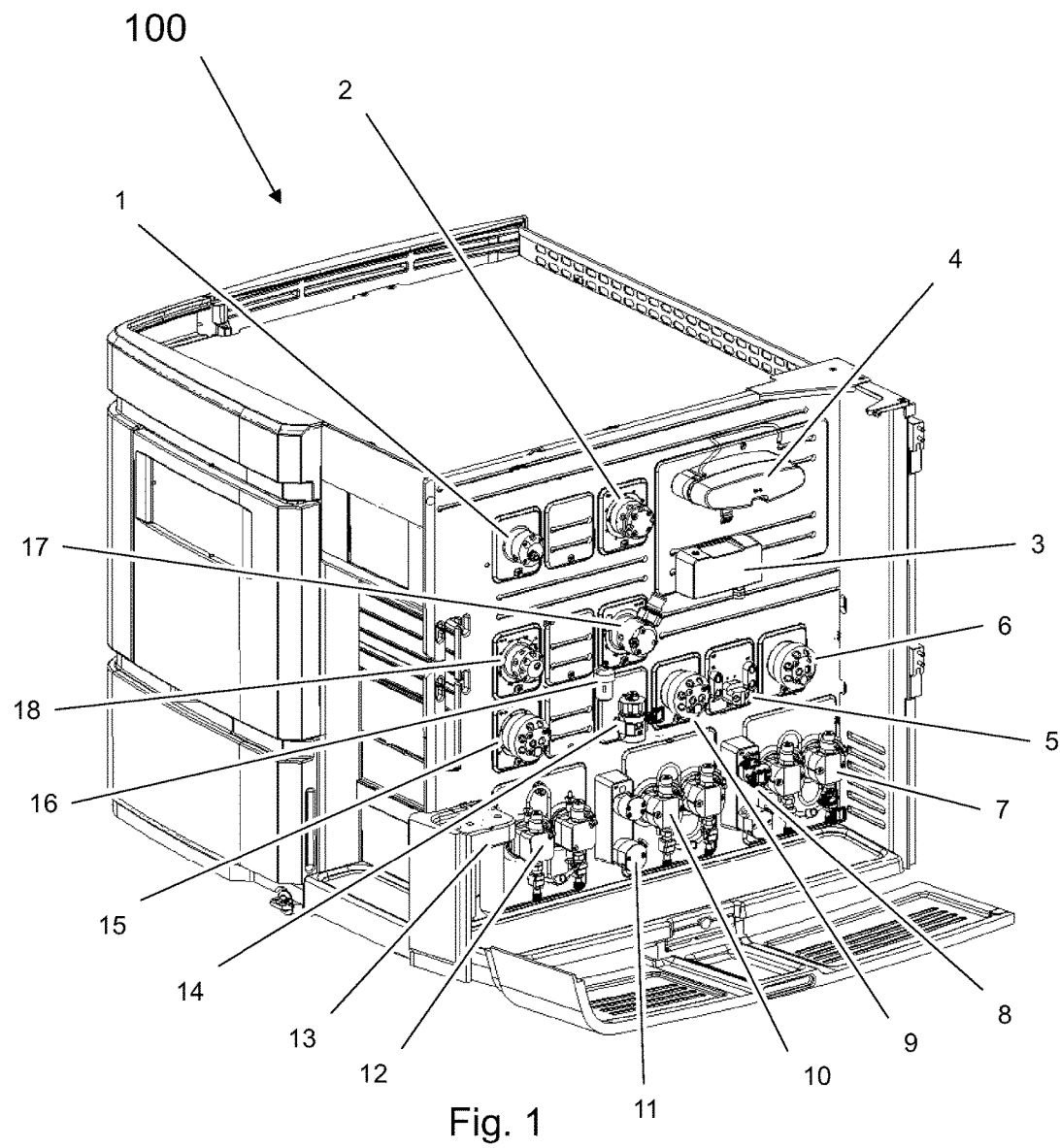
FIG. 1 shows one embodiment of a fluid handling system in the form of a liquid chromatography system, according to the present invention.

FIG. 1 shows one embodiment of an automated fluid handling system modular in the form of a liquid chromatography system, with a plurality of interchangeable modular components arranged in a liquid handling panel wherein the reference numbers denotes:
1. Injection valve
2. Column valve with integrated pressure sensors
3. Conductivity monitor
4. UV monitor
5. Quaternary valve
6. Inlet valve B with integrated air sensor
7. System pump
8. Pressure monitor, system pump
9. Inlet valve A with integrated air sensor
10. System pump 11. Pressure monitor, sample pump
12. Sample pump
13. Rinsing system
14. Mixer with online filter
15. Sample inlet valve with integrated air sensor
16. Flow restrictor
17. pH valve
18. Outlet valve The disclosed embodiment is supplied with three high precision pumps 7, 10, 12. There are two System pumps 7, 10, System pump A 10 and System pump B 7, and one Sample pump 12. The System pumps 7, 10 may be used individually, or in combination to generate isocratic or gradient elution in purification methods. The Sample pump 12 is dedicated for direct loading of sample onto a column, or for filling of sample loops.

Function of the Pumps:

Each pump module consists of two pump heads (not shown). The individual heads are identical but actuated in opposite phase to each other by individual stepper motors, controlled by a microprocessor. The two pistons and pump heads work alternately to give a continuous, low pulsation, liquid delivery. The flow rate of the two System pumps may be varied between about 0.001 ml/min and 25.000 ml/min and the maximum operating pressure is about 20 MPa. The flow rate of the Sample pump may e.g. be varied between 0.01 and 25 ml/min and according to one embodiment the maximum operating pressure is 10 MPa.

According to one embodiment, the plurality of fluid control valves of at least two different configurations are valves of rotary type. Such a motorized rotary valve may consist of a Valve head with a number of defined bores with channels to the inlet and outlet ports of the valve. The Rotary disc, mounted on the motor, has a number of defined channels. The pattern of channels of the Rotary disc together with the pattern and location of the ports of the Valve head, define the flow path and function of each type of valve. When the Rotary disc turns, the flow path in the valve changes.

One embodiment of fluid control valves are Inlet valves A and B (9, 6 respectively) that are used to select which buffers or samples to use in a run, and Sample inlet valve 15 that is located before Sample pump 12. Inlet valve A 9 1 is located before System pump A 10, Inlet valve B 6 is located before System pump B 10, and Sample inlet valve 15 is located before Sample pump 12. Inlet valve A and Inlet valve B are connected to another embodiment of a fluid control valve in the form of a Quaternary valve 5. The Quaternary valve is used for automatic buffer preparation, and for formation of quartenary gradients. The number of inlets can be increased by installing component modules with extra inlet valves. Inlet valve A and Inlet valve B enable automatic changing between different buffers and wash solutions, and can be used to generate gradients by mixing buffer A and buffer B. The air sensors integrated in Inlet valve A and Inlet valve B can be used to prevent introduction of air into the pumps and columns.

The Quarternary valve is used for automatic mixing of four different solutions. The Quaternary valve opens one inlet port at a time, and the different solutions are mixed in a Mixer 14 to form the desired buffer. The opening time in the switching valve is controlled by the system. The volume for each inlet port opening increases stepwise when the flow increases. To obtain a homogeneous buffer composition, one has to make sure to use a mixer chamber volume suitable for the flow rate of the method.

The Quaternary valve can be used to create a gradient using four different solutions simultaneously in any combination. The percentage of each solution is controlled by instructions in the method. It is possible to form gradients that changes the percentage of two, three or four solutions linearly over time. This is useful when advanced methods are developed.

The Sample inlet valve 15 enables automatic loading of different samples when using the Sample pump 12 to inject sample directly onto the column or to fill a sample loop. The Sample inlet valve has an inlet dedicated for buffer. This Buffer inlet is used in methods to fill the Sample pump with solution before sample is introduced. The Buffer inlet is also used to wash the Sample pump with buffer between runs. The air sensor integrated in the Sample inlet valve is e.g. used when sample is applied from a vessel onto a column by selecting Inject all sample using air sensor in the Sample application phase of a method. This function uses the Buffer inlet is used to finalize sample injection and to remove air from the Sample pump.

Still another embodiment of fluid control valve may be an Injection valve 1, which is used to direct sample onto the column. The valve enables usage of a number of different sample application techniques. A sample loop can be connected to the Injection valve and filled either automatically using the Sample pump or manually using a syringe. The sample can also be injected directly onto the column using the Sample pump.

Still another embodiment of fluid control valve may be a Column valve 2 that is used for connection of columns to the system, and to direct the flow onto the column Up to five columns can be connected to the disclosed embodiment of said valve simultaneously. The valve also has a built-in bypass capillary that enables bypassing of connected columns.

The number of column positions can be increased by installing an extra Column valve. Both top and bottom of each column shall be connected to the Column valve. The top of the column shall be connected to one of the A ports (e.g., 1A), and the bottom of the column shall be connected to the corresponding B port (e.g., 1B). The flow direction can be set either from the top of the column to the bottom of the column, Down flow, or from the bottom of the column to the top of the column, Up flow. In the default flow path of the Column valve the columns are bypassed. Pressure monitors that measures the actual pressure over the column are integrated into the inlet and outlet ports of the Column valve.

Still another embodiment of fluid control valve may be a pH valve 17 that has an integrated flow cell where a pH electrode can be installed. This enables in-line monitoring of pH during the run. A flow restrictor is connected to the pH valve and can be included in the flow path to generate a backpressure high enough to prevent formation of air bubbles in the UV flow cell. The pH valve is used to direct the flow to the pH electrode and to the flow restrictor, or to bypass one or both.

Still another embodiment of fluid control valve may be an Outlet valve 18 that is used to direct the flow to a Fraction collector (not shown), to any of e.g. 10 outlet ports, or to waste. The number of outlets can be increased by installing an extra Outlet valve.

A Mixer 14 may e.g. be located after System pump A and System pump B and before the Injection valve. The purpose of the Mixer is to make sure that the buffers from the System pumps are mixed to give a homogenous buffer composition. The Mixer has a built-in filter that prevents impurities from entering the flow path.

To fulfill a desired purpose, with the disclosed liquid chromatography system it is possible to adapt and extend the flow path in a simple and a flexible way. Up to three extra fluid control valves or the like can be installed using the free valve positions. Dummy modules are installed in these positions at delivery. To obtain an optional flow path, it is also possible to move the standard fluid control valves to other positions. There are also two types of extra air sensors available which can be installed before Sample inlet valve or after Injection valve.

In the configuration disclosed in FIG. 1, 7 inlets are available for each inlet valve. To increase the number of inlets, an extra inlet valve can be installed which increases the number of inlets to 14 for one of the valves. This optional configuration can be convenient for example when a larger number of samples will be used. There is also a general type of inlet valve, Valve X, which can be used to increase the number of inlets to for example the Quaternary valve.

In the configuration disclosed in FIG. 1 with one column valve, 5 column positions are available. To increase the number of column positions to 10, an additional column valve can be installed in the instrument. An application can be to evaluate a number of different columns in method optimization.

In the configuration disclosed in FIG. 1 with one outlet valve, 10 outlet positions are available. To increase the number of outlets, one or two extra outlet valves can be connected, adding up to a total of 21 or 32 outlet positions. This optional configuration is convenient when collecting a number of large fractions outside the fraction collector.

Optional modules are easy to install in the disclosed modular liquid chromatography system. The dummy module is removed with a hexagon wrench and a bus cable is disconnected. The bus cable is connected to the optional fluid control valve or the like which is assembled in the instrument. The module is then added to the System properties in the control software. The available optional modules may e.g. be pre-configured to give the desired function. However, the function of a valve may e.g. be changed by changing the Node ID.

Figure 2:
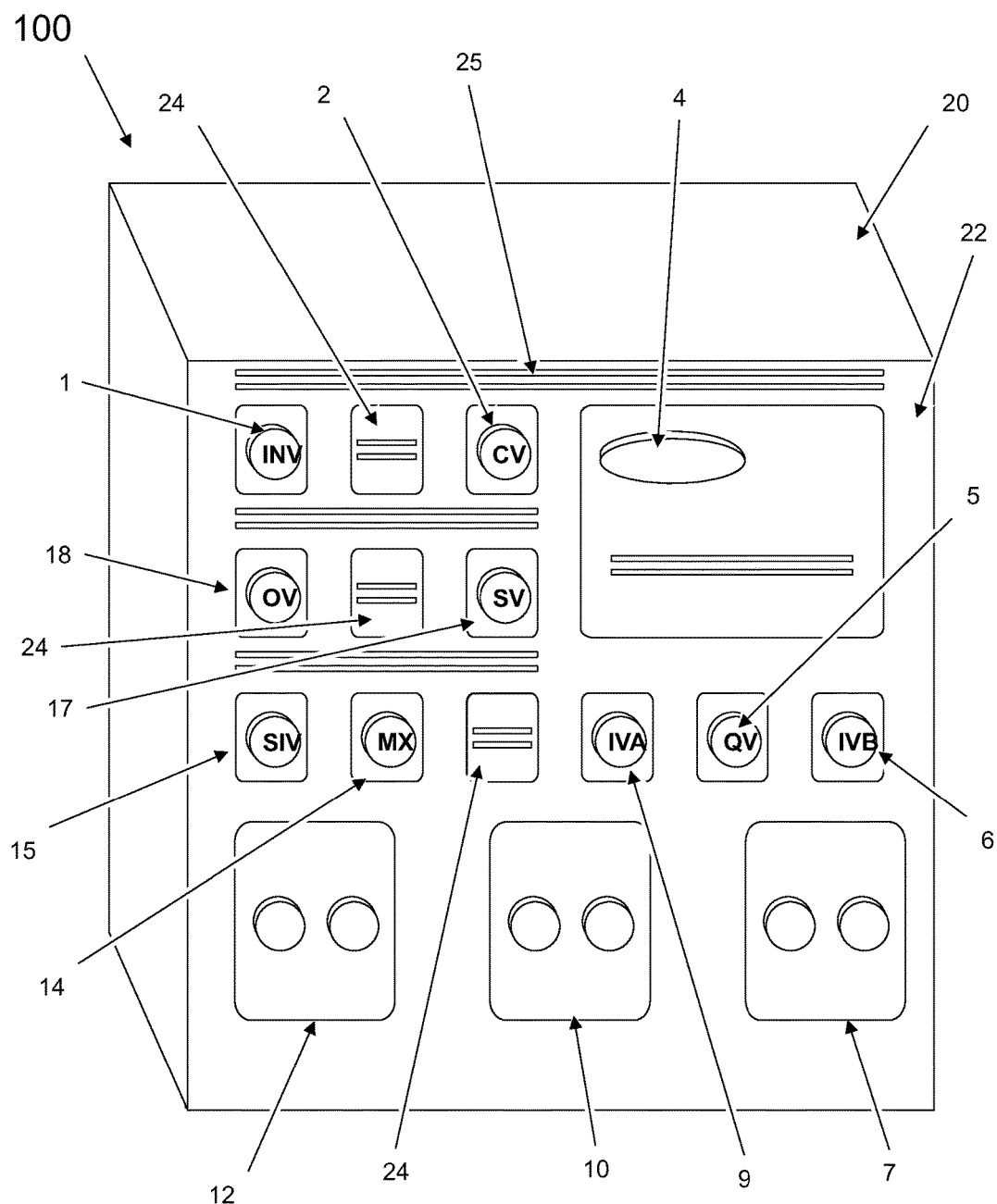
FIG. 2 is a schematic illustration of a housing with a liquid handling panel of the fluid handling system of FIG. 1.
Figure 3:
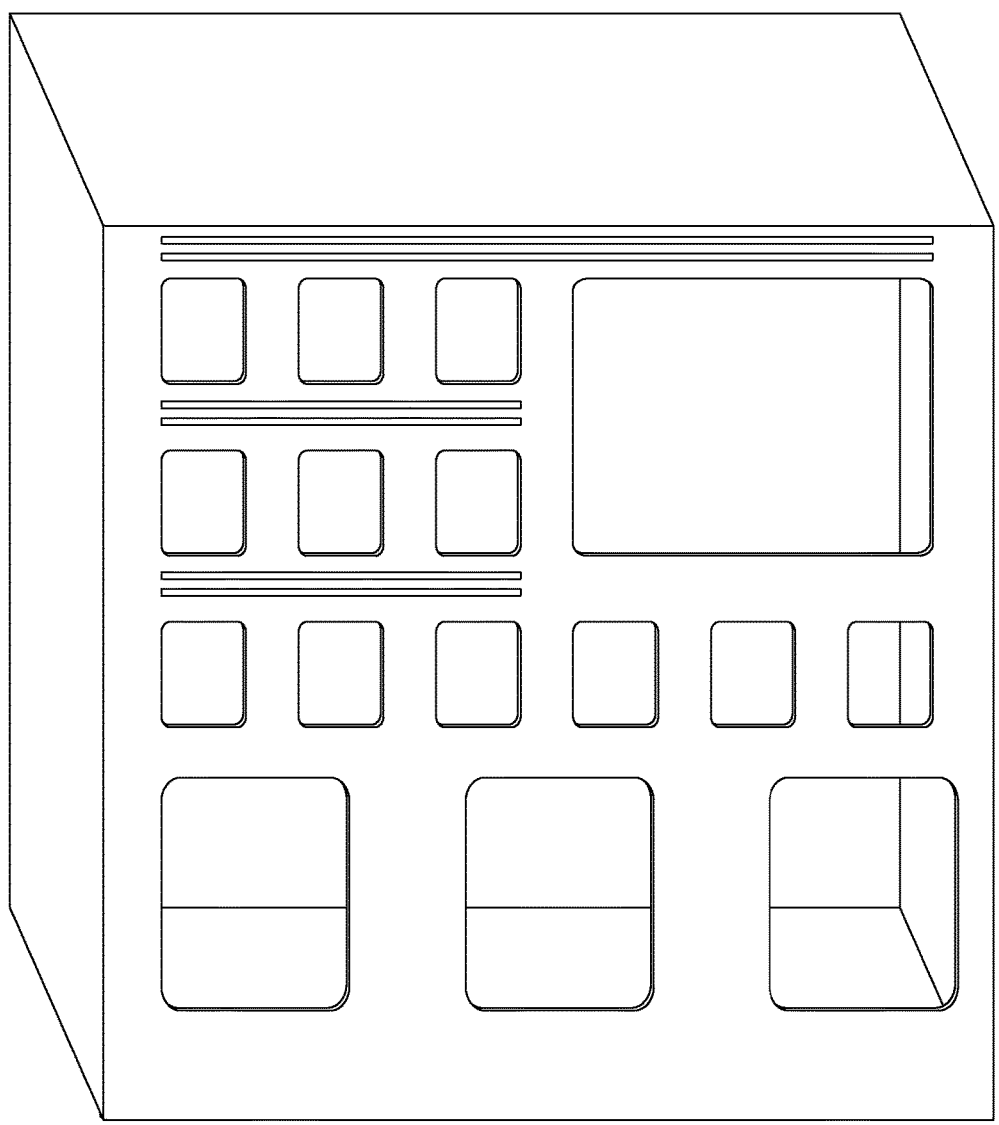
FIG. 3 is a schematic illustration of the housing with the liquid handling panel of FIG. 2 with the modular components of the fluid handling system removed.

FIG. 2 is a schematic illustration of a housing 20 with a liquid handling panel 22 of the fluid handling system in the form of a modular liquid chromatography system 100 of FIG. 1. In FIG. 2 some components have been removed for clarity reasons. In the disclosed configuration, as disclosed in detail above, the modular liquid chromatography system 100 comprises a plurality of fluid control valves in the form of: Injection valve 1, Column valve 2, Quaternary valve 5, Inlet valve B 6, Inlet valve A 9, Sample inlet valve 15, pH valve 17, and Outlet valve 18. The chromatography system 100 further comprises UV monitor 4, System pump B 7, System pump A 10, Sample pump 12, Mixer 14, and three Dummy modules 24. According to one embodiment, all liquid handling components and sensors arranged at the liquid handling panel 22 are designed to be readily interchangeable. The interchangeability provides improved service and upgrade possibilities and also a possibility to customize the positions of the respective liquid handling components, such as the fluid control valves, e.g. in order to optimize the fluid path for a specific experimental setup. As is illustrated in FIG. 2, there are three large component positions e.g. for pump modules, one UV-sensor position and 9 standard component positions, e.g. for fluid control valves or the like. The component positions are given a standardized size and shape to provide simple interchangeability. According to one embodiment, each modular component is retained in a mating component position by a single screw, and it is connected to the master control unit by a single bus cable providing both communication and system power to each component. FIG. 3 is a schematic illustration of the housing with the liquid handling panel of FIG. 2 with the modular components of the liquid chromatography system removed.

Figure 4A:
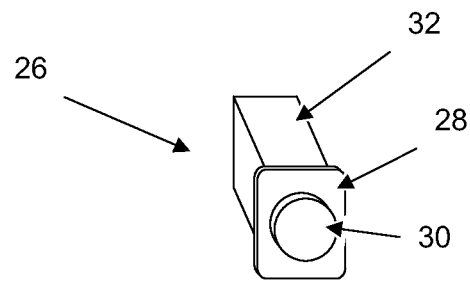
FIGS. 4a to 4d are schematic illustrations of examples of component modules of the fluid handling system removed.

FIGS. 4a to 4d are schematic illustrations of examples of fluid handling units in the form of modular component of the fluid handling system removed. FIG. 4a shows a standard interchangeable modular component 26, e.g. a fluid control valve or the like. The standard component module 26 comprises a panel member 28, an external fluidics section 30 and an internal non-fluidics section 32. According to one embodiment, the panel member 28 essentially separates the fluidics in the external fluidics section 30 from electronics and control means in the internal non-fluidics section 32.

Figure 4B:
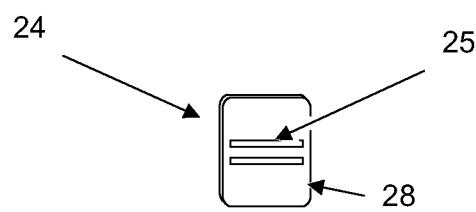
Figure 4C:
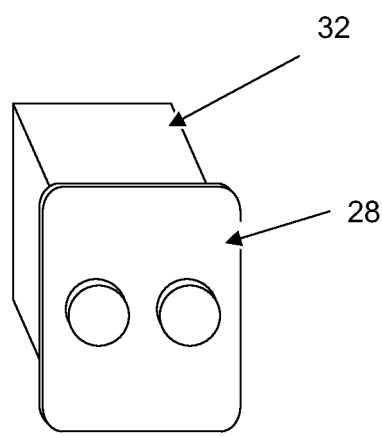
Figure 4D:
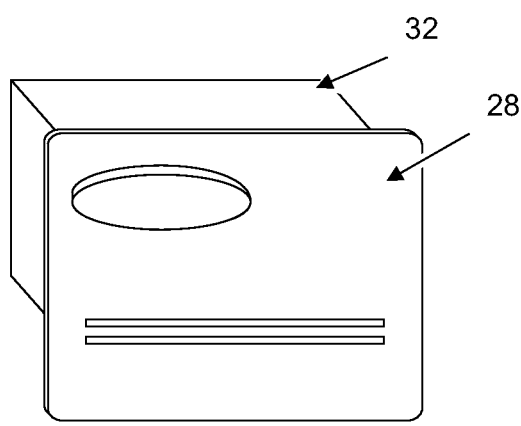

FIG. 4b shows a Dummy module 24, which is intended to be placed in non used standard component positions. In the disclosed embodiment, the Dummy modules are provided with mounting grooves for attachment of accessories to the system. In the disclosed embodiment the dummy module is shown as a panel member 28 without any internal section FIGS. 4c and 4d shows a pump module and an UV-module, respectively, each having an external fluidics section 30 and an internal non-fluidics section 32.

As is disclosed in FIGS. 4a to 4d, the interchangeable modular components 26 comprises a panel member arranged to separate the fluidics section from the non fluidics section and for attachment to a component position in the liquid handling panel. Said panel attachment member may be arranged so that all fluid connections of said modular component are arranged on a wet side of the panel attachment member separating them from electrical components that are arranged on a dry side thereof, hence providing a high degree of liquid resistance at the external part of the fluid handling panel, and so that the liquid resistance requirements for the internal sections may be somewhat lightened. According to one embodiment, the interchangeable modular components are sealed against the liquid handling panel by a sealing member. According to another embodiment, not shown, the modular component does not comprise any panel member, but there is provided a suitable sealing arrangement between the component position openings of the liquid handling panel and the external surface of the interchangeable modular components 26. In the disclosed embodiments, the component position openings of the liquid handling panel and the interchangeable modular components 26 are shown to have an essentially rectangular crosssectional shape, but other shapes may be equally applicable. According to one embodiment, there is provided a general fluid handling system comprising a housing and two or more fluid handling units arranged as interchangeable modular components as is schematically disclosed in FIG. 5a. As discussed above such a system may be configured for essentially any type of automated liquid handling operations provided that suitable fluid handling units are provided as interchangeable modular components for the system. According to one embodiment there is provided an automated fluid handling system comprising at least one fluid pump, at least one sensor unit and two or more fluid control valves of at least two different configurations, wherein at least the fluid control valves are arranged as interchangeable modular components.

The liquid handling panel 22 of the fluid handling system may e.g. be designed in any suitable manner to allow the modular components to be arranged in an efficient manner.

Figure 5A:
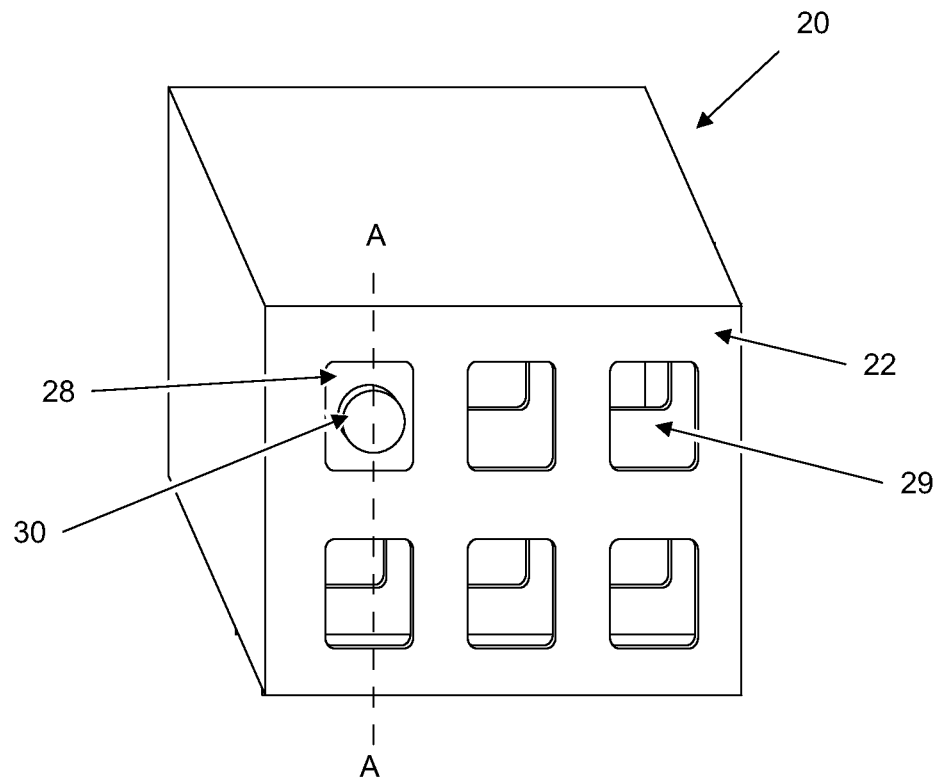
FIGS. 5a and 5b show a schematic embodiment of an automated fluid handling system.
Figure 5B:
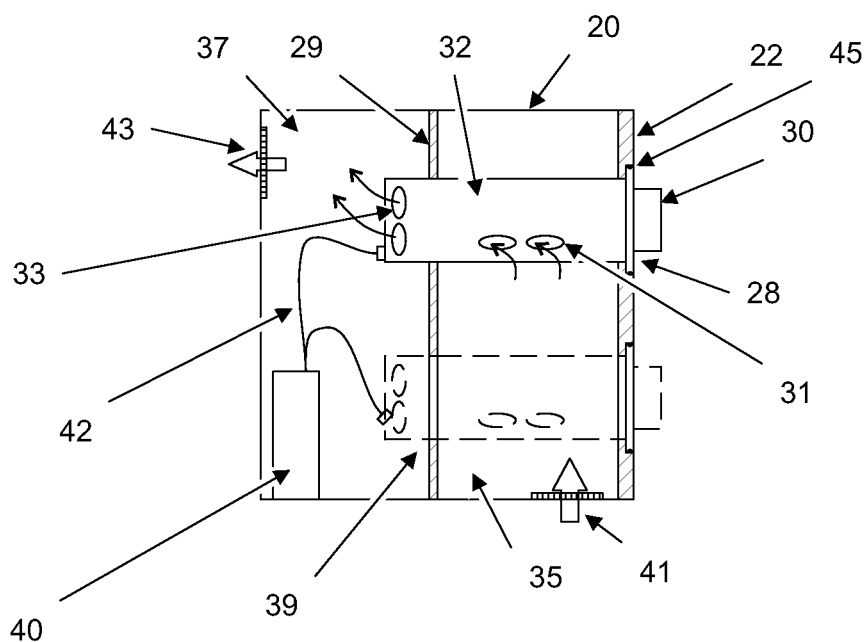

FIGS. 5a and 5b shows a schematic embodiment of an automated fluid handling system wherein the housing 20 comprises an internal climate panel 29 arranged at a distance behind the liquid handling panel 22 defining an air inlet compartment 35 and air outlet compartment 37 in the housing 20, the climate panel 29 being provided with complementary component positions 39 for receiving the internal non fluidics section 32 of the interchangeable modular components 26, and wherein the non-fluidics section 32 of at least one interchangeable modular component is provided with one or more air inlet openings 31 located in the air inlet compartment 35 and one or more air outlet openings 33 located in the air outlet compartment 37 when the interchangeable modular component arranged in position in the component position. FIG. 5b shows the fluid handling system of FIG. 5a in a schematic cross sectional view. As is indicated by inlet vent 41 and outlet vent 43, air for cooling interchangeable modular components 26 provided with air inlet and outlet openings 31, 33 is preferably arranged to enter the air inlet compartment 35 at a distance from the outlet vent 43 in order to avoid recirculation of air. The air circulation in the system may be achieved by a system cooling unit (not shown) providing a flow of air from the air inlet compartment 35 to the air outlet compartment 37, through the at least one interchangeable modular component 26. Alternatively, the at least one interchangeable modular component 26 is provided with a local cooling unit (not shown) providing a flow of air from the air inlet compartment 35 to the air outlet compartment 37. As is indicated, the complementary component positions 39 are arranged to provide a relatively air flow tight fit with respect to the internal non fluidics section 32 of the interchangeable modular components 26, and according to one embodiment, this may be achieved by a sealing arrangement. In FIG. 5b, there is shown a sealing member 45 for sealing the interchangeable modular components 26 with respect to the liquid handling panel 22, as discussed above. Other sealing member arrangements may be envisaged by a person skilled in the art. According to one embodiment, fluids are strictly restricted to the fluidics section 30 of the interchangeable modular component 26, but in alternative embodiments, only fluid connections are restricted to the fluidics section 30 allowing fluid to "cross" the fluid handling panel inside the non-fluidics section 30 of the interchangeable modular component 26.

In FIG. 5b there is further shown a master control unit 40 and buss connectors 42 for connecting the interchangeable modular components 26 to the master control unit 40. According to one embodiment, the component positions including the buss connectors 42 and the interchangeable modular components 26 are of plug and play configuration with respect to each other.

Figure 6:
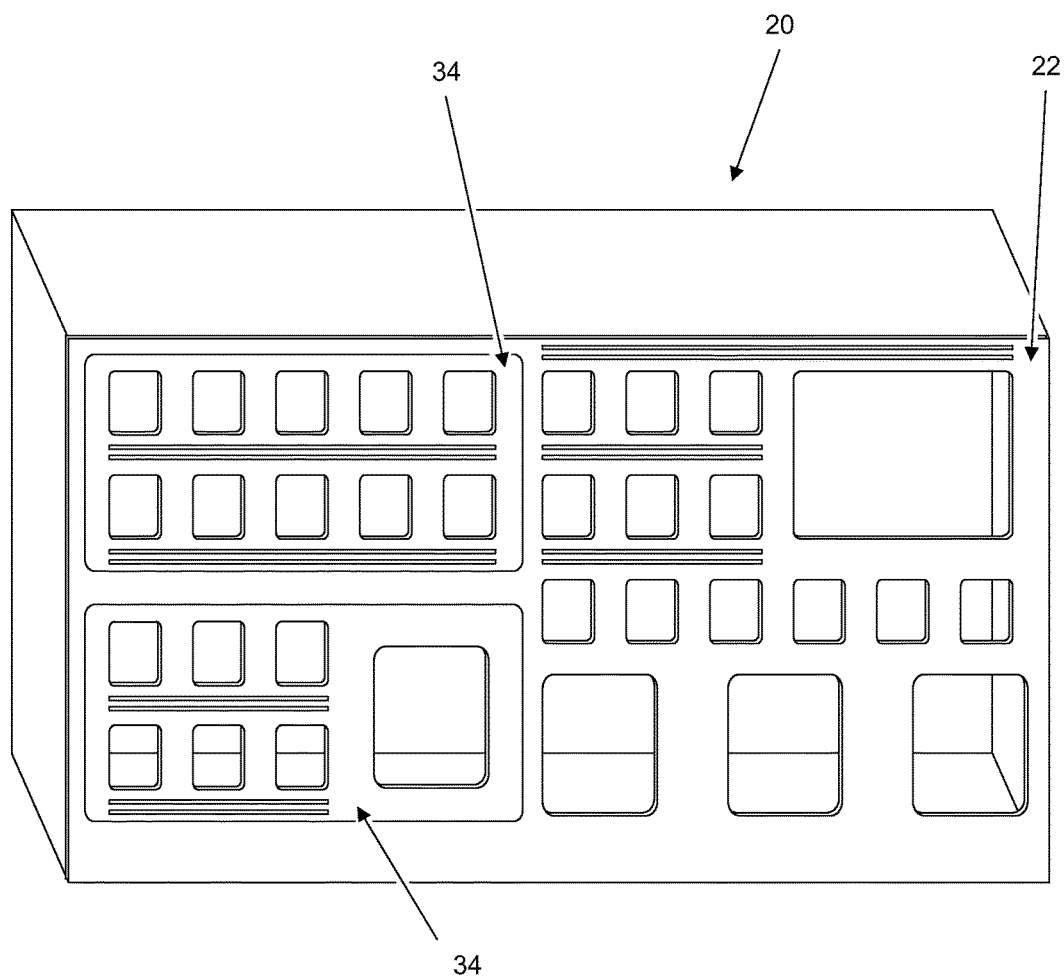
FIG. 6 is a schematic illustration of an embodiment of a housing with a modular liquid handling panel with the modular components of the fluid handling system removed.

FIG. 6 is a schematic illustration of an embodiment of a housing 20 with a modular liquid handling panel 22 with the modular components of the liquid chromatography system removed. In the disclosed embodiment, also the layout of the liquid handling panel 22 is configurable by means of two interchangeable panel sections 34 which may be selected in accordance with the desired layout of the system. In FIG. 6 two different layouts of the interchangeable panel sections are disclosed, but the layout may include any suitable configuration.

Figure 7A:
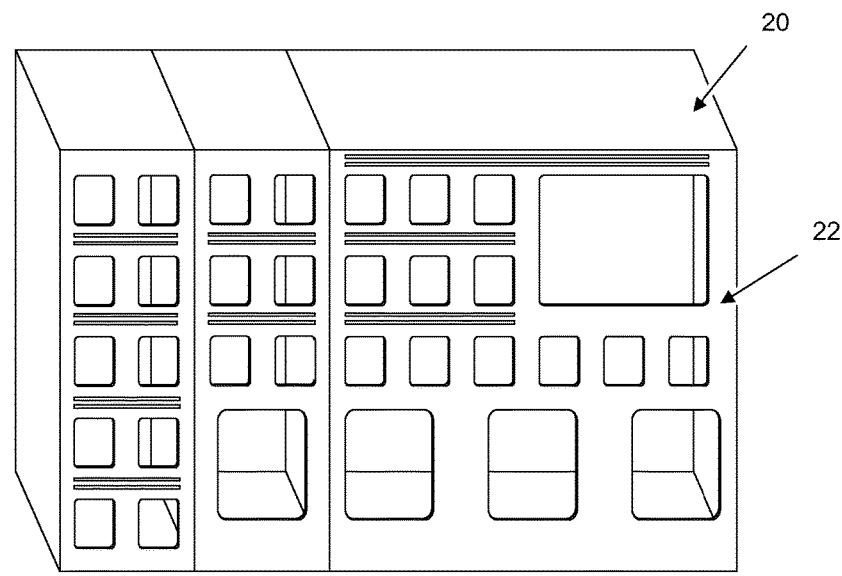
FIGS. 7a and 7b are schematic illustrations of an embodiment of a modular housing with a liquid handling panel with the modular components of the fluid handling system removed.
Figure 7B:
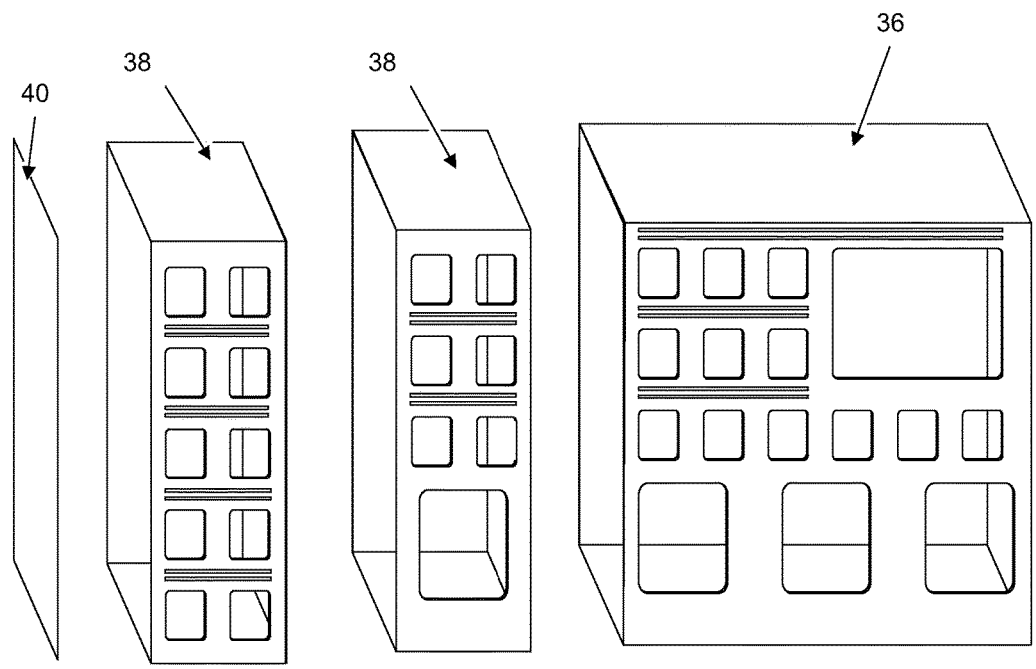

FIGS. 7a and 7b are schematic illustrations of an embodiment of a modular housing with a liquid handling panel with the modular components of the liquid chromatography system removed. In the disclosed embodiment, the modular housing is comprised of a main housing 36 that comprises the master control unit including power supply and climate control for the whole housing, two expansion housing modules 38 and a side member 40. This approach provides very flexible expansion possibilities for the chromatography system, while preserving the benefits of a single master control unit including power supply and climate control.

Figure 8:
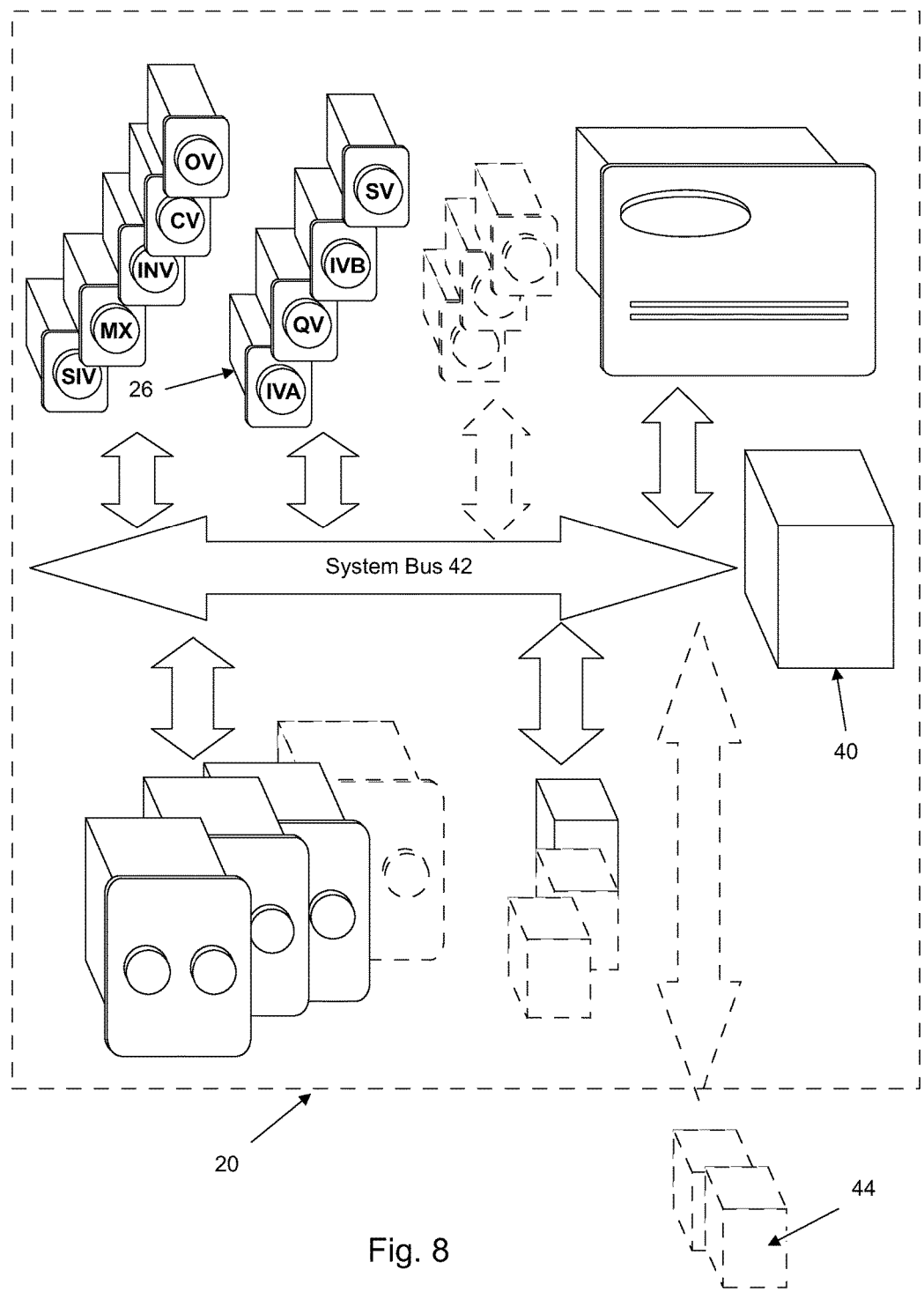
FIG. 8 is a schematic illustration of an embodiment of the system architecture of one embodiment of a fluid handling system according to the present invention.

FIG. 8 is a schematic illustration of an embodiment of the system architecture of one embodiment of a modular liquid chromatography system according to the present invention. As mentioned above, the chromatography system may comprise a master control unit 40 arranged to communicate with all modular components e.g. 1-26, over a system bus 42 such as a CAN-bus or the like. In one embodiment, each modular component is provided with a dedicated CPU unit allowing the component to independently perform operations in response to instructions over the BUS 42. In order to minimize the number of connectors to be attached to each modular component, the bus 42 further comprises power feed for the modular components. The Bus 42 may be connected to any suitable number of modular components arranged in the housing 20, but also to one or more modular components 44 outside of the housing 20 or the like. As is mentioned briefly above, the master control unit may further be arranged to control the climate in the housing. In addition to the disclosed modular components, other components of the chromatography system, e.g. a fraction collector or the like, may be arranged in the housing and the controlled climate therein.

According to one embodiment, different component modules are automatically identified by the master control unit, whereby they may be moved essentially freely between different positions. Moreover, the master control unit may be arranged to provide said information to Chromatography control software whereby experimental setup and planning may be performed. In one embodiment, the control system may be arranged to provide an optimized layout of the component modules with respect to the present layout of the liquid handling panel and available component modules for a specific experimental setup.

According to one embodiment, the interchangeable panel sections 34 of FIG. 5 and the expansion housing modules 38 of FIGS. 6a and 6b may be provided with means for automatic detection of the same to allow automatic configuration of the system by the master control unit 40. In one embodiment, each interchangeable panel section 34 and expansion housing module 38 comprises a hub (not shown) for connection to the system bus 42 in order to expand the system bus 42 network to the number of component modules in each interchangeable panel section 34 or expansion housing module 38.

Figure 9:
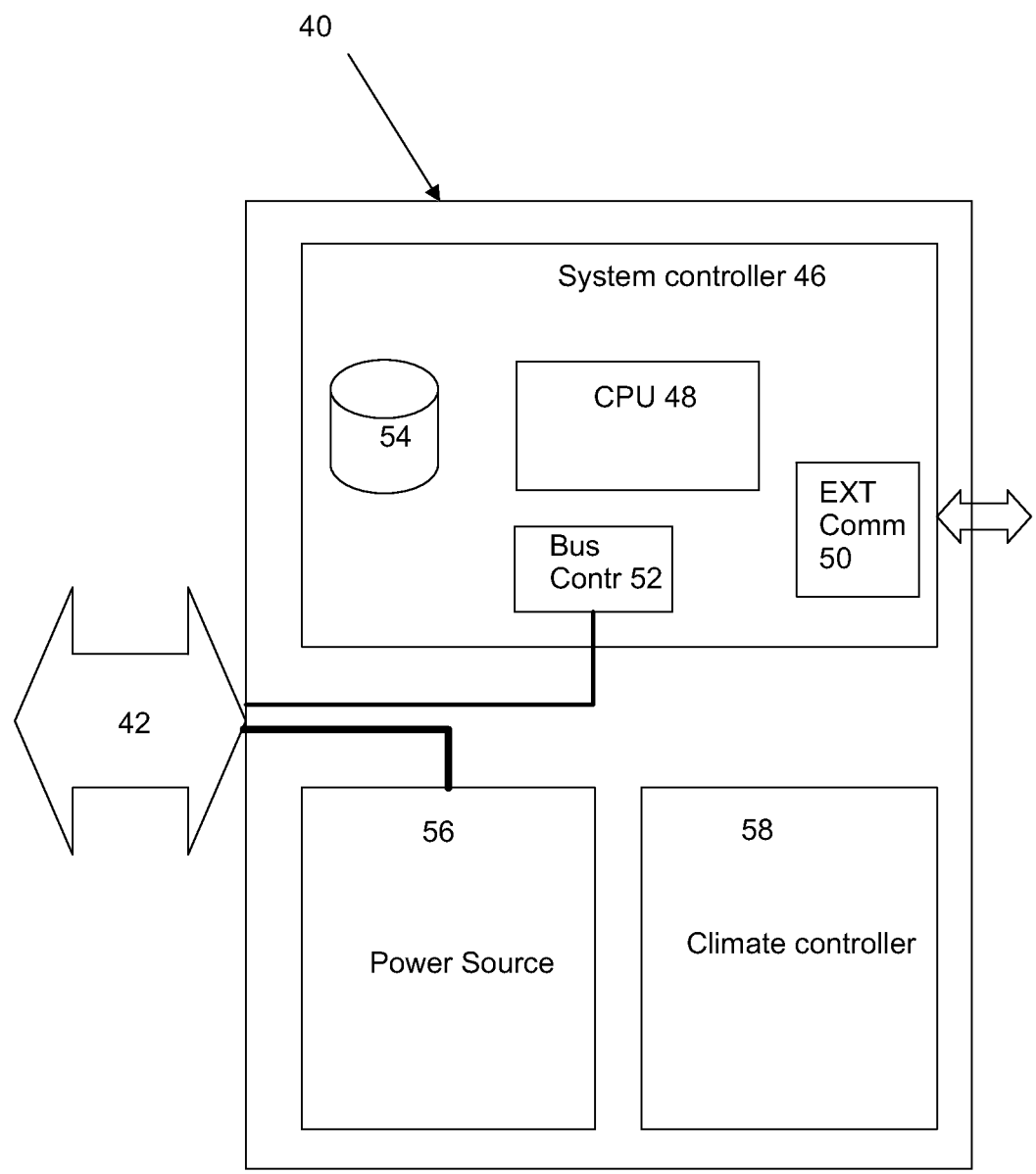
FIG. 9 is a schematic illustration of an embodiment of a master control unit of one embodiment of a fluid handling system according to the present invention.

FIG. 9 is a schematic illustration of an embodiment of a master control unit of one embodiment of a modular liquid chromatography system according to the present invention. The master control unit 40 comprises a system controller 46 for communicating with internal and external components and control computers (not shown) etc. According to one embodiment, the system controller comprises a suitable CPU 48, a bus controller 52, an external communications controller 50, such as a LAN unit, and a storage device 54. The bus controller 52 is providing communication with the component modules. The master control unit may further comprise a Power supply 56 and a climate controller 58 arranged to keep the internal climate in the housing 20 at a predetermined level as discussed above.

Figure 10:
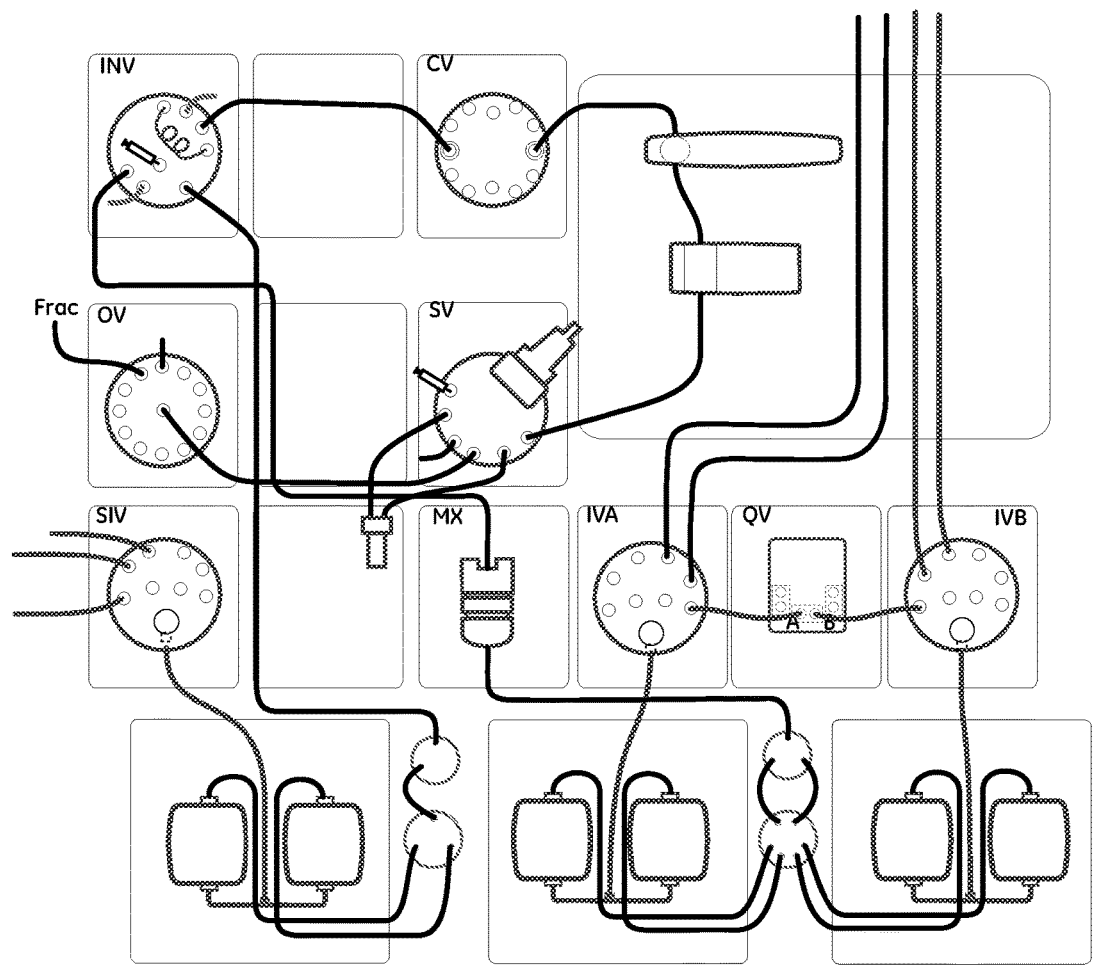
FIG. 10 is a schematic illustration of one embodiment of a fluidic interconnection arrangement between the modular components of the liquid handling panel for the liquid chromatography system of FIG. 1.

FIG. 10 is a schematic illustration of one embodiment of a fluidic interconnection arrangement between the modular components of the liquid handling panel. Taking into account the complexity of the disclosed interconnection arrangement, the benefit of optimizing the fluid paths in alternative configurations of the system becomes evident. The task of optimizing the fluid paths may e.g. be performed to reduce the total length/volume of the fluid paths/tubing arranged to interconnect the different component modules in the system. Alternatively the optimization may be performed to minimize the length/volume of one or more specific fluid paths, such as the sample output path from the column to the fraction collector, in order to minimize dispersion of the fractionized sample.

The invention claimed is:

1. An automated liquid chromatography system comprising:
    a housing;
    a master control unit connected to a system bus; and
    three or more fluid handling units arranged as interchangeable modular components comprising (i) an external fluidics section, (ii) an internal non-fluidics section including a bus connector for directly connecting the interchangeable modular component with the system bus, and (iii) a panel member arranged to separate the fluidics section from the non-fluidics section;
    wherein the housing comprises a liquid handling panel with at least four component receiving positions arranged in a two dimensional array and adapted to receive said interchangeable modular components such that, when inserted, the fluidics section is external to the housing and the non-fluidics section is internal to the housing;
    wherein each component receiving position includes a complementary connector for connecting the bus connector of the interchangeable modular component inserted therein to said system bus;
    wherein each interchangeable modular component includes a dedicated CPU unit allowing the interchangeable modular component to independently perform operations in response to instructions over the system bus;
    wherein the master control unit is arranged to automatically identify interchangeable modular components;
    wherein said housing is adapted to accommodate at least one pump, at least one sensor unit and at least two fluid control valves of different configurations, of which at least three of the pump, the sensor unit, and the fluid control valves are interchangeable modular components; and
    wherein the system is capable of performing automated liquid chromatography.

2. The chromatography system of claim 1, wherein the interchangeable modular components are sealed against the liquid handling panel by a sealing member.

3. The chromatography system of claim 1, wherein the interchangeable modular components are all of the same size.

4. The chromatography system of claim 1, wherein the interchangeable modular components are of two or more sizes.

5. The chromatography system of claim 1, wherein the liquid chromatography system further comprises a pH electrode that is external to the housing.

6. The chromatography system according to claim 5, wherein the at least two fluid control valves include an injection valve, a column valve with integrated pressure sensors, a quaternary valve, an inlet valve, a sample inlet valve, a pH valve, or an outlet valve.

7. The chromatography system according to claim 5, wherein the pH electrode is connected to a pH valve formed as an interchangeable modular component.

8. The chromatography system according to claim 7, wherein the pH valve includes an integrated flow cell for in-line monitoring of pH levels.

9. The chromatography system of claim 1, wherein the liquid chromatography system further comprises at least one expansion housing module arranged to be attached to the housing and for accommodating additional interchangeable modular components.

10. The chromatography system of claim 1, wherein the liquid chromatography system comprises two double piston pumps, one injection valve for injecting sample onto a column connecting a flow path of the liquid chromatography system, a UV monitor, and a mixer, wherein the pumps, valve, monitor, and mixer are interchangeable modular components.

11. The chromatography system of claim 10, wherein the liquid chromatography system further comprises a column valve comprising pressure sensors integrated into inlet and outlet ports of the column valve for measuring the actual pressure over the connected column.

12. The chromatography system of claim 10, wherein the liquid chromatography system further comprises a sample inlet valve.

13. The chromatography system of claim 10, wherein the liquid chromatography system further comprises a conductivity monitor.

14. The chromatography system of claim 10, wherein the liquid chromatography system further comprises at least one expansion housing module arranged to be attached to the housing and for accommodating additional interchangeable modular components.

15. The chromatography system according to claim 1, wherein the at least two fluid control valves include an injection valve, a column valve with integrated pressure sensors, a quaternary valve, an inlet valve, a sample inlet valve, a pH valve, or an outlet valve.

16. The chromatography system of claim 1, wherein the liquid chromatography system includes two double piston pumps, one injection valve for injecting a sample onto a column connected to a flow path of the liquid chromatography system, a UV monitor, a mixer, a pH-valve with an integrated flow cell for in-line monitoring of pH levels, and a quaternary valve for automatic buffer preparation and formation of quaternary gradients, wherein the pumps, injection valve, monitor, mixer, pH valve, and quaternary valve are interchangeable modular components.

17. An automated liquid chromatography system comprising:
    a housing;
    a master control unit connected to a system bus; and
    two or more fluid handling units arranged as interchangeable modular components comprising a panel member arranged to separate a fluidics section from a non-fluidics section, wherein the fluidics section of each interchangeable modular component comprises one or more fluid connectors for connecting the fluid handling unit to a liquid chromatography fluid path and wherein all fluid connectors are on an external side of the panel member, said liquid chromatography fluid path being reconfigurable by moving the interchangeable modular components freely between the component receiving positions, and wherein the non-fluidics section includes a bus connector for directly connecting the interchangeable modular components to the system bus;

wherein the housing comprises a liquid handling panel with two or more component receiving positions adapted to receive said interchangeable modular components such that, when inserted, the fluidics section is external to the housing and the non-fluidics section is internal to the housing;

wherein each component receiving position includes a complementary connector for connecting the bus connector of the interchangeable modular component inserted therein to said system bus;

wherein each interchangeable modular component includes a dedicated CPU unit allowing the interchangeable modular component to independently perform operations in response to instructions over the system bus;

wherein the master control unit is arranged to automatically identify interchangeable modular components;

wherein said housing is adapted to accommodate at least one pump, at least one sensor unit and at least two fluid control valves of different configurations, of which at least two of the pump, the sensor unit, and the fluid control valves are interchangeable modular components; and wherein the system is capable of performing automated liquid chromatography.

18. The chromatography system of claim 17, wherein the interchangeable modular components are all of the same size.

19. The chromatography system of claim 17, wherein the interchangeable modular components are of two or more sizes.

20. The chromatography system of claim 17, wherein the two or more component receiving positions are arranged in a two dimensional array.

21. The chromatography system of claim 17, wherein the housing comprises at least four component receiving positions.

22. The chromatography system of claim 17, wherein the liquid chromatograph system further comprises a pH electrode that is external to the housing.

23. The chromatography system according to claim 22, wherein the at least two fluid control valves include an injection valve, a column valve with integrated pressure sensors, a quaternary valve, an inlet valve, a sample inlet valve, a pH valve, or an outlet valve.

24. The chromatography system according to claim 22, wherein the pH electrode is connected to a pH valve formed as an interchangeable modular component.

25. The chromatography system according to claim 24, wherein the pH valve includes an integrated flow cell for in-line monitoring of pH levels.

26. The chromatography system of claim 17, wherein the liquid chromatography system further comprises at least one expansion housing module arranged to be attached to the housing and for accommodating additional interchangeable modular components.

27. An automated liquid chromatography system comprising:

a housing;

a master control unit connected to a system bus; and two or more fluid handling units arranged as interchangeable modular components comprising a panel member arranged to separate a fluidics section from a non-fluidics section, wherein the fluidics section of each interchangeable modular component comprises one or more fluid connectors for connecting the fluid handling unit to a liquid chromatography fluid path and wherein all fluid connectors are on an external side of the panel member, said liquid chromatography fluid path being reconfigurable by moving the interchangeable modular components freely between the component receiving positions, and wherein the non-fluidics section includes a bus connector for directly connecting the interchangeable modular components to the system bus;

wherein the housing comprises a liquid handling panel with at least four component receiving positions arranged in a two dimensional array and adapted to receive said interchangeable modular components such that, when inserted, the fluidics section is external to the housing and the non-fluidics section is internal to the housing;

wherein each component receiving position includes a complementary connector for connecting the bus connector of the interchangeable modular component inserted therein to said system bus;

wherein each interchangeable modular component includes a dedicated CPU unit allowing the interchangeable modular component to independently perform operations in response to instructions over the system bus;

wherein the master control unit is arranged to automatically identify interchangeable modular components;

wherein said housing is adapted to accommodate at least one pump, at least one sensor unit and at least two fluid control valves of different configurations, of which at least two of the pump, the sensor unit, and the fluid control valves are interchangeable modular components; and wherein the system is capable of performing automated liquid chromatography.

28. The chromatography system of claim 27, wherein the interchangeable modular components are all of the same size; or of two or more sizes.

29. The chromatography system of claim 27, wherein the system further comprises at least one expansion housing module arranged to be attached to the housing and for accommodating additional interchangeable modular components.

30. The chromatography system of claim 27, wherein the system further comprises a pH electrode that is external to the housing, and wherein the pH electrode is connected to a pH valve formed as an interchangeable modular component.

* * * * *